United States Patent [19]

Saita et al.

[11] Patent Number: 5,449,783
[45] Date of Patent: Sep. 12, 1995

[54] DIPHENYLTHIAZOLE DERIVATIVE

[75] Inventors: Masaru Saita, Saga; Hisataka Inoue, Kurume; Kouichi Ikesue, Saga; Noriyuki Fujimoto, Tosu; Ikuo Shinohara, Tosu; Taniguchi: Yasuaki, Tosu; Yoshiki Deguchi, Tosu; Hidenao Minami; Kanji Noda, both of Chikushino, all of Japan

[73] Assignee: Hisamitsu Pharmaceutical Co., Inc., Tosu, Japan

[21] Appl. No.: 108,572

[22] PCT Filed: Mar. 7, 1992

[86] PCT No.: PCT/JP91/00310

§ 371 Date: Aug. 23, 1993

§ 102(e) Date: Aug. 23, 1993

[87] PCT Pub. No.: WO92/15570

PCT Pub. Date: Sept. 17, 1992

[51] Int. Cl.[6] .................. C07D 277/44; C07D 277/52
[52] U.S. Cl. ..................................... 548/197; 548/195
[58] Field of Search ........................ 548/193, 195, 197

[56] References Cited

FOREIGN PATENT DOCUMENTS 03173876  7/1991  Japan .
04173782  6/1992  Japan .
1188846   4/1970  United Kingdom .
9215970   9/1992  WIPO .

Primary Examiner—Robert Gerstl
Attorney, Agent, or Firm—Bucknam and Archer

[57] ABSTRACT

A novel diphenythiazole derivative represented by the following general formula (I):

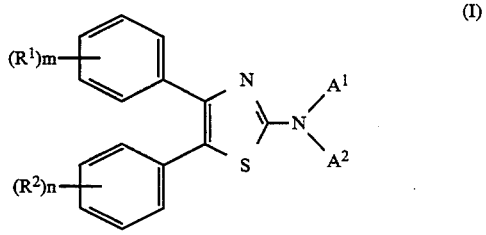

wherein m and n are each 1 or 2; $R^1$ and $R^2$ represent each a hydrogen atom, a lower alkyl group, a lower alkoxy group, a lower alkylsulfenyl group, a nitro group, an amino group, a methanesulfonyloxy group or a halogen atom; $A^1$ represents a lower alkanesulfonyl group, a halogenated lower alkanesulfonyl group, a substituted benzenesulfonyl group, a lower acyl group or a halogenated lower acyl group; and $A^2$ represents a hydrogen atom, a lower alkanesulfonyl group, a halogenated lower alkanesulfonyl group or a lower alkyl group, and being efficacious as a drug having antiinflammatory, analgesic, antiallergic, uricosuric or platelet aggregation inhibiting effects.

6 Claims, No Drawings

DIPHENYLTHIAZOLE DERIVATIVE

This application is a 371 of PCT/JP91/00310 filed Mar. 7, 1992.

1. Technical Field

This invention relates to novel diphenylthiazole derivative which are efficacious as a drug having antiinflammatory, analgesic, antiallergic, uricosuric or platelet aggregation inhibiting effects.

2. Background Art

There have been disclosed compounds having an amino group or an amino substituent at the 2-position of a diphenylthiazole parent nucleus in Japanese Patent Laid-Open Gazette No. (Sho) 50-121269 (121269/1978) (hereinafter referred to as the prior reference A), Japanese Patent Laid-Open Gazette No. (Sho) 54-160369 (160369/1979) (hereinafter referred to as the prior reference B), Japanese Patent Laid-Open Gazette No. (Sho) 58-216186 (216186/1983) (hereinafter referred to as the prior reference C) and Japanese Patent Laid-Open Gazette No. (Hei) 3-27370 (27370/1991) (hereinafter referred to as the prior reference D).

For example, compounds including 2-morpholino-4,5-diphenylthiazole, 2-methylamino-4,5-diphenylthiazole and 2-(N-methyl-N-acetyl)amino-4,5-diphenylthiazole are described in the prior reference A. Regarding the pharmacological effects of these compounds, the prior reference A states that they have a platelet aggregation inhibiting effect accompanied by a hypocholesterolemic effect but exhibit weak or scarcely any antiinflammatory and analgesic effects.

In the prior reference B, compounds including 2-phenethylamino-4,5-diphenylthiazole, 5-methyl-2-phenethylamino-4-phenylthiazole and 2-furfurylamino-5-methyl-4-phenylthiazole are described. The prior reference B states that these compounds are efficacious as an antiinflammatory agent or an immunomodulator.

The prior reference C describes about guanidino-thiazole derivatives. It is stated therein that these compounds are particularly efficacious as chemical affecting lipid metabolism, an antithrombotic drug and as a fungicide.

Furthermore, the prior reference D discloses thiazole compounds having pharmacological effects such as antithrombotic and vasodilating effects, processes for producing these compounds and pharmaceutical compositions containing the same.

However these prior references neither disclose nor suggest any diphenylthiazole derivative which is mono- or disubstituted at the amino group at the 2-position by a substituted sulfonyl residue, an acyl group or a halogen-substituted acyl group, like the compound of the present invention. As a matter of course, it has not been known at all hitherto that such compounds have excellent pharmacological activities relating to antiinflammatory, analgesic, antiallergic, uricosuric or platelet aggregation inhibiting effects.

Although the thiazole compound described in the prior reference D is partly common to the compound of the present invention regarding a fundamental parent nucleus and substituted phenyl groups at the 4 and 5-positions and has a chemical structure relatively similar to that of the compounds of the present invention, the former differs from the latter in the substituent at the 2-position. Namely, the compounds of the prior reference D has a substituent

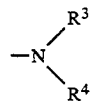

at the 2-position wherein $R^3$ and $R^4$ represent each a hydrogen atom, a lower alkyl group optionally having a heterocyclic group or a piperidyl group optionally having appropriate substituents. In contrast, the group $A^1$ of the compounds of the present invention comprises a substituted sulfonyl group, an acyl group or a halogen-substituted acyl group. Thus the compounds of the present invention differ from the the prior reference D in the employed substituent. Any desired pharmacological effect on a satisfactory level cannot be achieved by using such compounds as the ones described in the prior reference D.

Although acidic nonsteroidal antiinflammatory drugs, typical examples of which include aspirin and indomethacin, have clear effects as compared with basic antiinflammatory drugs, they have side effects of causing, for example, gastrointestinal tract disorders. When these drugs are to be administered to young or aged persons or to patients with chronic inflammation over a prolonged period of time, it is therefore unavoidable under the existing circumstances to take a measure to relieve these side effects.

DISCLOSURE OF THE INVENTION

Thus, it is an object of the present invention to develop a highly safe antiinflammatory drug having an improved antiinflammatory effect and relieved side effects and to develop an antiallergic drug, a remedy for gout or a platelet aggregation inhibitor.

The present inventors have continued studies in order to develop a drug having excellent antiinflammatory, analgesic, antiallergic, platelet aggregation inhibiting and uricosuric effects and relieved side effects. As a result, they have found out that the certain diphenylthiazole derivatives satisfy the above-mentioned requirements, thus completing the present invention.

Accordingly, the present invention relates to diphenylthiazole derivatives represented by the following general formula (I):

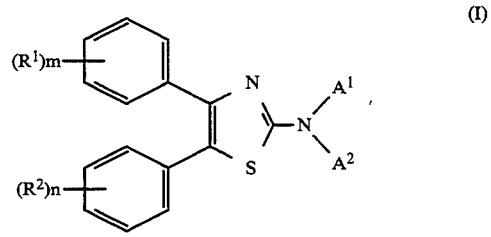

wherein m and n are each 1 or 2; $R^1$ and $R^2$ represent each a hydrogen atom, a lower alkyl group, a lower alkoxy group, a lower alkylsulfenyl group, a nitro group, an amino group, a methanesulfonyloxy group or a halogen atom; $A^1$ represents a lower alkanesulfonyl group, a halogenated lower alkanesulfonyl group, a substituted benzenesulfonyl group, a lower acyl group or a halogenated lower acyl group; and $A^2$ represents a hydrogen atom, a lower alkanesulfonyl group, a halogenated lower alkanesulfonyl group or a lower alkyl group, and pharmaceutically acceptable salts thereof.

Now the above general formula (I) will be described in greater detail.

The lower alkyl group referes to an alkyl group having from 1 to 6 carbon atoms, such as methyl, ethyl, n-propyl, iso-propyl, n-butyl, iso-butyl, t-butyl, n-pentyl and n-hexyl groups.

The lower alkoxy group refers to an alkoxy group having from 1 to 6 carbon atoms, such as methoxy, ethoxy, n-propoxy, iso-propoxy, n-butoxy, iso-butoxy and t-butoxy groups.

The lower alkylsulfenyl group refers to an alkylsulfenyl group having from 1 to 6 carbon atoms, such as methylsulfenyl, ethylsulfenyl, n-propylsulfenyl, iso-propylsulfenyl, n-butylsulfenyl, iso-butylsulfenyl and t-butylsulfenyl groups.

The lower alkanesulfonyl group refers to an alkanesulfonyl group having from 1 to 6 carbon atoms, such as methanesulfonyl, ethane and butanesulfonyl groups.

The halogenated lower alkanesulfonyl group refers to a lower alkanesulfonyl group substituted by one or more halogen atoms.

The lower acyl group refers to an acyl group having from 1 to 6 carbon atoms, such as formyl, acetyl, propionyl and butyryl groups.

The halogenated lower acyl group refers to a lower acyl group substituted by one or more halogen atoms.

Halogen atoms refers to fluorine, chlorine, bromine and iodine atoms.

Examples of the pharmaceutically acceptable salts include alkali metal salts such as lithium, sodium and potassium salts, alkaline earth metal salts such as calcium and magnesium salts, inorganic salts such as ammonium salt and organic salts such as triethylamine, ethanolamine, triethanolamine, dicyclohexylamine and glutamic acid salts, though the present invention is not restricted thereto.

When the compounds represented by the general formula (I) or a salt thereof are used as a drug, they may be formulated, either as such or together with well-known fillers, into appropriate preparations such as tablet, capsule, injection, suppository, ointment, cream, gel, lotion, aerosol, buccal, plaster, fomentation or eye lotion and can be stably administered either orally or parenterally.

The dose is appropriately determined depending on, for example, the conditions, age and sex of the subject. In the case of oral administration to an adult, it is usually preferable that the compound (I) or its salt is administered in a single dose of 1 to 300 mg once to thrice a day.

Now processes for producing the compound of the present invention will be described. The compounds of the present invention can be obtained in a high yield by the processes as will be given hereinbelow, though the process for producing the compound of the present invention is not restricted thereto.

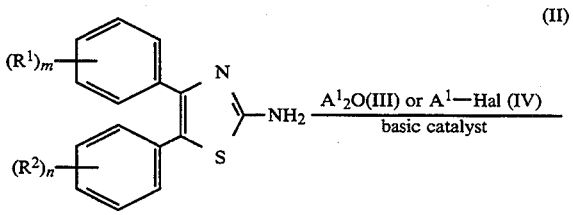

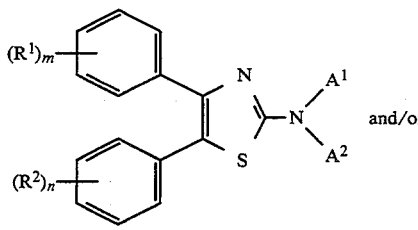

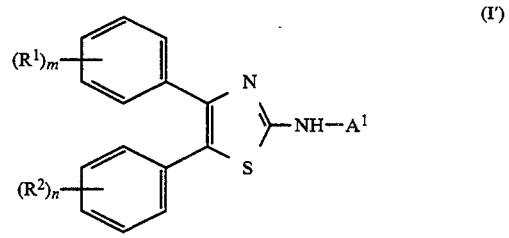

wherein m, $R^1$, $R^2$, $A^1$ and $A^2$ are as defined above; and Hal represents a halogen atom.

The reaction proceeds as follows. A compound represented by the general formula (II) is reacted with a compound represented by the general formula (III) or (IV) in an appropriate solvent in the presence of a basic catalyst under cooling, at room temperature or under heating for 0.5 to 30 hours. Thus a compound represented by the general formula (I) or (I') can be obtained. In the above general formula (I), $A^2$ and $A^1$ represent one and the same group, while in the above general formula (I'), the hydrogen atom corresponds to $A^2$.

As the reaction solvent, an inert organic solvent such as dichloromethane, chloroform, carbon tetra-chloride, tetrahydrofuran, N,N-dimethylformamide, N,N-dimethylacetamide or dimethyl sulfoxide may be used without restriction. As the basic catalyst, a basic substance capable of promoting the deacidification such as pyridine, collidine, triethylamine, tri-n-propylamine or tri-n-butylamine may be used, though the present invention is not restricted thereto.

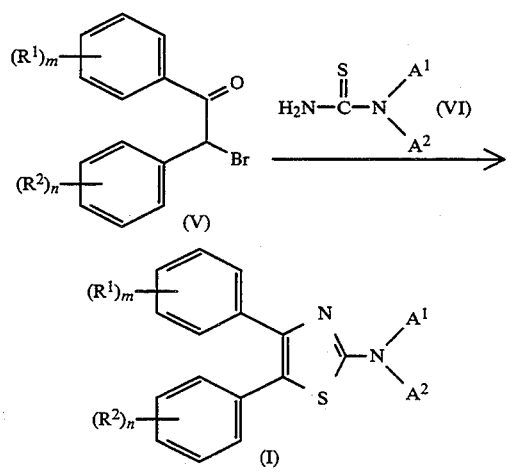

wherein m, n, $R^1$, $R^2$, $A^1$ and $A^2$ are as defined above.

The reaction proceeds as follows. A compound represented by the general formula (V) is mixed with a compound represented by the general formula (VI) in an appropriate solvent at room temperature or under heating. Thus a compound represented by the general formula (I) can be obtained.

As the reaction solvent, methanol, ethanol, tetrahydro-furan, N,N-dimethylformamide or dimethyl sulfoxide may be used, though the present invention is not restricted thereto.

EXAMPLES

To further illustrate the present invention in greater detail and not by way of limitation, the following Example will be given.

Example 1

53.7 g of anhydrous trifluoromethanesulfonic acid was slowly dropped into a solution of 30 g of 2-amino-4,5-diphenythiazole and 15.6 g of triethylamine in chloroform under stirring at $-20°$ to $-15°$ C., and the resulting mixture was stirred as such for 1.5 hours. The reaction mixture was poured into ice-water and extracted. The extract was successively washed with 1 N hydrochloric acid, a saturated aqueous solution of sodium hydrogencarbonate and water in this order and dried over anhydrous magnesium sulfate. After distilling off the solvent under reduced pressure, the crystals thus formed were recovered by filtration and recrystalized from isopropyl ether/ethyl acetate to give 18.2 g of 2-trifluoromethanesulfonylamino-4,5-diphenylthlazole. The melting point of this product was from 212° to 214° C.

IR: 3248, 1323 cm$^{-1}$. MS (m/e): 384 (M+). Elemental analysis (as $C_{16}H_{11}F_3N_2O_2S_2$): calculated: C 49.99%, H 2.88%, N 7.29%. found: C 49.98%, H 2.92%, N 7.37%.

Example 2

15.9 g of anhydrous trifluoromethanesulfonic acid was slowly dropped into a solution of 5.0 g of 2-amino-4-(4-methylphenyl)-5-phenylthiazole and 5.2 ml of triethylamine in chloroform under stirring in a nitrogen atmosphere at $-20°$ to $-15°$ C., and the resulting mixture was stirred as such for 2 hours. Then the reaction mixture was successively washed with diluted hydrochloric acid, a saturated aqueous solution of sodium hydrogencarbonate and water in this order and dried over anhydrous magnesium sulfate. After distilling off the solvent under reduced pressure, the reaction product was separated with a silica gel column by using chloroform/ethyl acetate as a developer. The crystals thus obtained were recrystallized from n-hexane/isopropyl ether/ethyl acetate to give 2.8 g of 2-trifluoromethanesulfonylamino-4-(4-methylphenyl)-5-phenylthiazole. The melting point of this product was from 186.5° to 188.5° C.

IR: 3188, 1325 cm$^{-1}$. MS (m/e): 398 (M+). Elemental analysis (as $C_{17}H_{13}F_3N_2O_2S_2$): calculated: C 51.25%, H 3.29%, N 7.03%. found: C 51.35%, H 3.42%, N 7.08%.

Example 3

13.5 g of anhydrous trifluoromethanesulfonic acid was slowly dropped into a solution of 5.0 g of 2-amino-4,5-bis(4-methoxyphenyl)thiazole and 5.0 ml of triethylamine in chloroform under stirring in a nitrogen atmosphere at $-20°$ to $-15°$ C., and the resulting mixture was stirred as such for 2 hours. Then the reaction mixture was successively washed with diluted hydrochloric acid, a saturated aqueous solution of sodium hydrogencarbonate and water in this order and dried over anhydrous magnesium sulfate. After distilling off the solvent under reduced pressure, the reaction product was separated with a silica gel column by using chloroform/ethyl acetate as a developer. The crystals thus obtained were recrystallized from isopropyl ether/ethyl acetate to give 1.9 g of 2-trifluoromethanesulfonylamino-4,5-bis(4-methoxy-phenyl)thiazole. The melting point of this product was from 240° to 242° C.

IR: 3300–2900, 1344 cm$^{-1}$. MS (m/e): 444 (M+). Elemental analysis (as $C_{18}H_{15}F_3N_2O_4S_2$): calculated: C 48.64%, H 3.40%, N 6.30%. found: C 48.66%, H 3.42%, N 6.34%.

Example 4

2.68 ml of anhydrous trifluoromethanesulfonic acid was slowly dropped into a solution of 2.88 g of 2-amino-4,5-bis(4-fluorophenyl)thiazole and 1.8 ml of triethylamine in chloroform under stirring in a nitrogen atmosphere at $-20°$ to $-15°$ C., and the resulting mixture was stirred as such for 1 hour. Then the reaction mixture was successively washed with diluted hydrochloric acid, a 5% aqueous solution of sodium hydrogencarbonate and water in this order and dried over anhydrous magnesium sulfate. After distilling off the solvent under reduced pressure, the reaction product was separated with a silica gel column by using isopropyl ether as a developer. The crystals thus obtained were recrystallized from petroleum ether/diethyl ether to give 0.47 g of 2-trifluoromethanesulfonylamino-4,5-bis(4-fluorophenyl)thiazole. The melting point of this product was from 193° to 195° C.

IR: 3210, 1340 cm$^{-1}$. MS (m/e): 420 (M+). Elemental analysis (as $C_{16}H_9F_5N_2O_2S_2$): calculated: C 45.72%, H 2.16%, N 6.66%. found: C 45.69%, H 2.24%, N 6.48%.

Example 5

2.5 g of methanesulfonyl chloride was dropped into a solution of 5.0 g of 2-amino-4,5-diphenylthiazole and 3.3 ml of pyridine in dichloromethane under stirring at room temperature, and the resulting mixture was stirred as such overnight. Then the reaction mixture was successively washed with diluted hydrochloric acid, a saturated aqueous solution of sodium hydrogencarbonate and water in this order and dried over anhydrous magnesium sulfate. After distilling off the solvent under reduced pressure, the reaction product was separated with a silica gel column by using isopropyl ether and ethyl acetate as a developer. The crystals thus obtained were recovered by filtration from isopropyl ether and washed with diethyl ether to give 1.6 g of 2-methanesulfonylamino-4,5-diphenylthiazole. The melting point of this product was from 225° to 227° C.

IR: 3206, 1278 cm$^{-1}$.

MS (m/e): 330 (M+). Elemental analysis (as $C_{16}H_{14}N_2O_2S_2$): calculated: C 58.16%, H 4.27%, N 8.48%. found: C 57 96%, H 4 33% N 8.41%.

Example 6

2.70 g of chloromethanesulfonyl chloride was dropped into a solution of 2.27 g of 2-amino-4,5-diphenylthiazole in pyridine under stirring at room temperature, and the resulting mixture was stirred as such for 2 hours. Then the reaction mixture was poured into ice-water and the crystals thus precipitated were recovered by filtration and separated with a silica gel column by using isopropyl ether and ethyl acetate as a developer. The crystals thus obtained were recrystallized from isopropyl ether/ethyl acetate to give 1.45 g of 2-chloromethanesulfonylamino-4,5-diphenylthiazole. The melting point of this product was from 201° to 203° C.

IR: 3215, 1305, 1290 cm$^{-1}$. MS (m/e): 364 (M+). Elemental analysis (as $C_{16}H_{13}ClN_2O_2S_2$): calculated: C 52.67%, H 3.59%, N 7.68%. found: C 52.67%, H 3.49%, N 7.58%.

Example 7

0.92 g of 2,2,2-trifluoroethanesulfonyl chloride was dropped into a solution of 1:56 g of 2-amino-4,5-bis(4-methoxyphenyl)thiazole in pyridine under stirring at room temperature in a nitrogen atmosphere, and the resulting mixture was stirred as such for 1 hour. Then the reaction mixture was poured into ice-water and the crystals thus precipitated were recovered by filtration and recrystallized from diethyl ether/ethyl acetate to give 0.80 g of 2-(2,2,2-trifluoroethanesulfonyl)amino-4,5-bis(4-methoxyphenyl)thiazole. The melting point of this product was from 259° to 261° C.

IR: 3210, 1330 cm$^{-1}$. MS (m/e): 458 (M+). Elemental analysis (as $C_{19}H_{17}N_2O_4S_2$): calculated: C 49.78%, H 3.74%, N 6.11%. found: C 49.52%, H 3.59%, N 5.93%.

Example 8

3.12 g of 2-amino-4,5-diphenylthiazole and 2.44 g of 4-trifluoromethylbenzenesulfonyl chloride were stirred in pyridine at room temperature for 4.5 hours. Then the reaction mixture was poured into ice-water and the crystals thus precipitated were recovered by filtration and recrystallized from isopropyl ether/ethyl acetate to give 0.55 g of 2-(4-trifluoromethylbenzenesulfonyl)amino-4,5-diphenylthiazole. The melting point of this product was from 248° to 249° C.

IR: 3195, 1320 cm$^{-1}$. MS (m/e): 460 (M+). Elemental analysis (as $C_{22}H_{15}N_2O_2S_2$): calculated: C 57.38%, H 3.28%, N 6.08%. found: C 57.31%, H 3.39%, N 5.95%.

Example 9

2.88 g of 2-amino-4,5-bis(4-fluorophenyl)thiazole was heated under reflux in anhydrous trifluoroacetic acid for 1 hour. The reaction mixture was evaporated to dryness under reduced pressure and the crystals thus formed were recovered by filtration from n-hexane and washed to give 3.56 g of 2-trifluoroacetamino-4,5-bis(4-fluorophenyl)thiazole. The melting point of this product was from 214° to 216° C.

IR: 2878, 1644 cm$^{-1}$. MS (m/e): 384 (M+). Elemental analysis (as $C_{17}H_9F_9N_2OS$): calculated: C 53.13%, H 2.36%, N 7.29%. found: C 52.984, H 2.44%, N 7.05%.

Examples 10 to 46

In accordance with the procedures of the above Examples 1 to 9, the compounds of the present invention as listed in Table 1 were synthesized.

TABLE 1

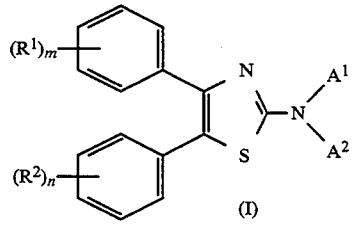

(I)

| Ex. No. | $R^1$ | $R^2$ | $A^1, A^2$ | m.p. (°C.) |
| --- | --- | --- | --- | --- |
| Ex. No. 10 | 4-CH$_3$O | H | SO$_2$CF$_3$, H | 219~221 |
| Ex. No. 11 | 4-CH$_3$O | 4-Cl | SO$_2$CF$_3$, H | 164~165 (dec.) |
| Ex. No. 12 | H | 4-Cl | SO$_2$CF$_3$, H | 202~204 |
| Ex. No. 13 | 4-Cl | 4-Cl | SO$_2$CF$_3$, H | 221~222 |
| Ex. No. 14 | 4-F | H | SO$_2$CF$_3$, H | 176~178 |
| Ex. No. 15 | 4-F | 3-F | SO$_2$CF$_3$, H | 165~167 |
| Ex. No. 16 | H | 3-F | SO$_2$CF$_3$, H | 215~217 |
| Ex. No. 17 | H | 4-NO$_2$ | SO$_2$CF$_3$, H | 212.5~215 |
| Ex. No. 18 | H | 4-NH$_2$ | SO$_2$CF$_3$, H | 216~218 |
| Ex. No. 19 | 4-CH$_3$O | 4-CH$_3$O | SO$_2$CH$_3$, H | 208~210 |
| Ex. No. 20 | 4-F | 4-F | SO$_2$CH$_3$, H | 222~224 |
| Ex. No. 21 | H | 4-NO$_2$ | SO$_2$CH$_3$, H | 233~235 |
| Ex. No. 22 | 4-F | 4-F | SO$_2$CH$_3$, SO$_2$CH$_3$ | 213~215 |
| Ex. No. 23 | H | 4-NO$_2$ | SO$_2$CH$_3$, SO$_2$CH$_3$ | 203~205 |
| Ex. No. 24 | 4-CH$_3$SO$_2$O | H | SO$_2$CH$_3$, SO$_2$CH$_3$ | 199~201 |
| Ex. No. 25 | H | H | SO$_2$CH$_2$CF$_3$, H | 192~194 |
| Ex. No. 26 | 4-F | 4-F | SO$_2$CH$_2$CF$_3$, H | 207~209 |
| Ex. No. 27 | H | H | SO$_2$—⌬—Cl, H | 268~270 |
| Ex. No. 28 | H | H | COCF$_3$, H | 240~242 |
| Ex. No. 29 | 4-CH$_3$ | H | SO$_2$CF$_3$, H | 186.5~188.5 |
| Ex. No. 30 | H | 4-CH$_3$ | SO$_2$CF$_3$, H | 210.5~212 |
| Ex. No. 31 | 4-CH$_3$ | 4-CH$_3$ | SO$_2$CF$_3$, H | 216.5~217 |
| Ex. No. 32 | H | 4-CH$_3$O | SO$_2$CF$_3$, H | 188~190 |
| Ex. No. 33 | 4-NO$_2$ | H | SO$_2$CF$_3$, H | 228~230 |
| Ex. No. 34 | 4-CH$_3$O | 4-F | SO$_2$CF$_3$, H | 222~224 |
| Ex. No. 35 | H | 2-F | SO$_2$CF$_3$, H | 184~185 |

TABLE 1-continued

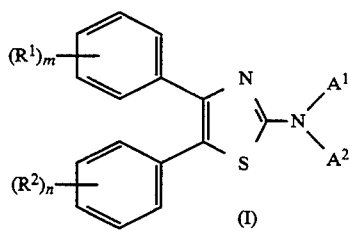

(I)

| Ex. No. | R¹ | R² | A¹, A² | m.p. (°C.) |
|---|---|---|---|---|
| Ex. No. 36 | H | 3-F | SO$_2$CF$_3$, H | 214~217 |
| Ex. No. 37 | H | 4-F | SO$_2$CF$_3$, H | 197~198.5 |
| Ex. No. 38 | 4-F | 3-F | SO$_2$CF$_3$, H | 165~167 |
| Ex. No. 39 | H | 2,4-diF | SO$_2$CF$_3$, H | 176~177.5 |
| Ex. No. 40 | H | 3,4-diF | SO$_2$CF$_3$, H | 190.5~192 |
| Ex. No. 41 | 4-Cl | H | SO$_2$CF$_3$, H | 223~225 |
| Ex. No. 42 | H | H | SO$_2$CF$_3$, CH$_2$CH$_3$ | 124~125.5 |
| Ex. No. 43 | H | H | COCH$_3$, H | 221~222.5 |
| Ex. No. 44 | 4-F | 4-F | SO$_2$CH$_2$CF$_3$, H | 207~209 |
| Ex. No. 45 | 4-F | 4-F | COCF$_3$, H | 213~216 |
| Ex. No. 46 | 4-CH$_3$S | H | SO$_2$CF$_3$, H | 212~215 |

[Function]

To demonstrate the drug effects of the compounds according to the present invention, pharmacological experiments using each of the compounds of the present invention and pharmacological data thus obtained will be given.

Pharmacological experiment 1
Rat (carrageenin-induced paw edema experiment A)

Male Wistar rats weighing 140 to 160 g were divided into groups each comprising 8 animals.

0.1 ml of 1% carrageenin (PICNIN A, mfd. by Zushi Kagaku K.K.) was subcutaneously injected into the right hind paw of each rat and the edema thus induced was measured with the lapse of time by using a device for measuring foot edema. A test compound was suspended in a 0.5% CMC solution and orally administered to the rat 1 hour before the injection of carrageenin. The results expressed in the inhibition ratio (average) of each test group to the control group, to which no compound had been orally administered, 3 hours after the induction of the reaction are given in Table 2.

TABLE 2

| Test compound | Dose (mg/kg) | Inhibition ratio (%) |
|---|---|---|
| cpd. of Ex. 1 | 10 | 44.9 |
| cpd. of Ex. 10 | 10 | 46.8 |
| cpd. of Ex. 17 | 10 | 23.9 |
| cpd. of Ex. 32 | 10 | 52.3 |
| cpd. of Ex. 37 | 10 | 56.2 |

Pharmacological experiment 2
Rat (carrageenin-induced paw edema experiment B)

Male Wistar rats weighing 140 to 160 g were divided into groups each comprising 8 animals.

0.1 ml of 1% carrageenin (PICNIN A, mfd. by Zushi Kagaku K.K.) was subcutaneously injected into the right hind paw of each rat and the edema thus induced was measured with the lapse of time by using a device for measuring foot edema. A test compound was suspended in a 60% N,N-dimethylformamide solution in physiological saline and intravenously injected to the rat immediately before the injection of carrageenin. The results expressed in the inhibition ratio (average) of each test group to the control group, to which no compound had been orally administered, 3 hours after the induction of the reaction are given in Table 3.

TABLE 3

| Test compound | Dose (mg/kg) | Inhibition ratio (%) |
|---|---|---|
| cpd. of Ex. 1 | 1 | 41.3 |
| cpd. of Ex. 10 | 1 | 52.8 |
| cpd. of Ex. 17 | 1 | 36.6 |
| cpd. of Ex. 32 | 1 | 48.1 |
| cpd. of Ex. 37 | 1 | 46.4 |
| indomethacin | 1 | 47.4 |

Pharmacological experiment 3
Rat (carrageenin-induced paw edema experiment C)

Male Wistar rats weighing 160 to 170 g were divided into groups each comprising 7 animals.

0.1 ml of 1% carrageenin (PICNIN A, mfd. by Zushi Kagaku K.K.) containing a test compound was subcutaneously injected into the right hind paw of each rat and the edema thus induced was measured with the lapse of time by using a device for measuring foot edema. The results expressed in the inhibition ratio (average) of each test group to the control group, to which no compound had been orally administered, 3 hours after the induction of the reaction are given in Table 4.

TABLE 4

| Test compound | Dose (mg/kg) | Inhibition ratio (%) |
|---|---|---|
| cpd. of Ex. 1 | 0.003 | 44.2 |
| cpd. of Ex. 10 | 0.003 | 50.7 |
| cpd. of Ex. 17 | 0.003 | 37.1 |
| cpd. of Ex. 32 | 0.003 | 50.4 |
| cpd. of Ex. 37 | 0.003 | 49.8 |
| indomethacin | 0.03 | 44.7 |

Pharmacological experiment 4
(Rat adjuvant arthritis experiment)

0.1 ml of 6 mg/ml *Mycobacterium butyricum* suspension in liquid paraffin was intracutaneously injected into the tail root of each male Wistar rat weighing about 200 g. 20 days thereafter, rats clearly suffering from arthritis in the hind paw were selected and divided into groups each comprising 7 animals.

A test compound was orally administered in a dose as specified below once a day for 7 days. Then the effect of the test compound on the adjuvant arthritis was examined by using an inhibition ratio on the edema of the hind paw as an indicator. The inhibition ratio was calculated according to the following equation. Table 5 shows the results.

TABLE 5

$$\text{Inhibition ratio} = \frac{\text{(foot volume 27 days after intracutaneous administration)} - \text{(normal foot volume)}}{\text{(foot volume 20 days after intracutaneous administration)} - \text{(normal foot volume)}} \times 100$$

| Test compound | Dose (mg/kg) | Inhibition ratio (%) |
|---|---|---|
| cpd. of Ex. 1 | 10 | 36.6 |
| cpd. of Ex. 10 | 10 | 45.6 |
| cpd. of Ex. 17 | 10 | 35.3 |
| cpd. of Ex. 32 | 10 | 34.6 |
| cpd. of Ex. 37 | 10 | 44.9 |

Pharmacological experiment 5
(Mouse acetic acid-induced writhing experiment)

Male ddy mice weighing about 23 g were divided into groups each comprising 7 to 9 animals.

30 minutes after a test compound was orally administered, a 0.6% acetic acid solution in physiological saline was intraperitoneally administered in a dose of 0.1 ml per 10 g of the body weight. From 5 minutes after the intraperitoneal administration, the frequency of writhing was counted for 10 minutes to determine the inhibition ratio by comparing with the frequency of writhing in the control group. Table 6 summarizes the results.

TABLE 6

| Test compound | Dose (mg/kg) | Inhibition ratio (%) |
|---|---|---|
| cpd. of Ex. 1 | 20 | 24.6 |
| cpd. of Ex. 10 | 20 | 46.1 |
| cpd. of Ex. 17 | 20 | 36.3 |
| cpd. of Ex. 32 | 20 | 28.6 |
| cpd. of Ex. 37 | 20 | 18.1 |

Pharmacological experiment 6
(Effect of inhibiting biosynthesis of prostaglandin $E_2$)

To a tris buffer solution containing 50 mM of glutathione and 50 mM of epinephrine were added prostaglandin synthetase (originating in sheep seminal vesicle) and a test drug dissolved in DMSO and incubated for 10 minutes. Then the reaction was ceased with 1 N hydrochloric acid under ice-cooling and the reaction mixture was extracted with ethyl ether. Then the extract was solidified by drying with nitrogen gas, dissolved in ethanol and developed on a TLC with a developer. Then the aimed part was scraped up and the radioactivity was measured with a liquid scintillation counter. The results were expressed in the inhibition ratio (average) to the control group to which no compound had been administered. Table 7 shows the results.

TABLE 7

| Test compound | Dose (mg/kg) | Inhibition ratio (%) |
|---|---|---|
| cpd. of Ex. 1 | $10^{-7}$ | 45.5 |
| cpd. of Ex. 10 | $10^{-7}$ | 57.2 |
| cpd. of Ex. 17 | $10^{-7}$ | 48.1 |
| cpd. of Ex. 32 | $10^{-7}$ | 52.2 |
| cpd. of Ex. 37 | $10^{-7}$ | 43.9 |
| indomethacin | $10^{-5}$ | 43.9 |

Pharmacological experiment 7
(Effect of inhibiting biosynthesis of 5-HETE)

Hartley guinea pigs weighing 300 to 500 g were used.

0.2% oyster glycogen was intraperitoneally administered to each guinea pig and, after 16 hours, neutrophiles of the animal were harvested. To $3 \times 10^7$ cells/ml of the neutrophiles were added a test drug dissolved in DMSO and $2 \times 10^{-3}$M of indomethacin. After incubating for 2 minutes, 1 mg/ml of A 23187 and 2 $\mu$Ci of $^{14}$C-arachidonic acid were added and the incubation was continued for additional 2 minutes. After ceasing the reaction with 1N hydrochloric acid under ice-cooling, the reaction mixture was extracted with ethyl acetate. Then the extract was solidified by drying with nitrogen gas, dissolved in ethanol and developed on a TLC with a developer. Then the aimed part was scraped up and the radioactivity was measured with a liquid scintillation counter. The results were expressed in the inhibition ratio (average) to the control group to which no compound had been administered. Table 8 shows the results.

TABLE 8

| Test compound | Dose (mg/kg) | Inhibition ratio (%) |
|---|---|---|
| cpd. of Ex. 1 | $10^{-6}$ | 40.5 |
| cpd. of Ex. 10 | $10^{-6}$ | 45.1 |
| cpd. of Ex. 17 | $10^{-6}$ | 47.3 |
| cpd. of Ex. 32 | $10^{-6}$ | 44.8 |
| cpd. of Ex. 37 | $10^{-6}$ | 48.7 |
| NDGA* | $10^{-6}$ | 43.0 |
| indomethacin | $10^{-4}$ | 43.9 |

*nordihydroguairetic acid.

[Effects of the Invention]

As the carrageenin-induced rat plantar edema experiments A, B and C given in the above pharmacological experiments 1 to 3 clearly show, each compound of the present invention has a remarkable effect of inhibiting carrageenin-induced edema as compared with the comparative drug.

As the rat adjuvant arthritis experiment given in the above pharmacological experiment 4 clearly shows, each compound of the present invention has a remarkable effect of inhibiting adjuvant arthritis.

On the other hand, as the mouse acetic acid-induced writhing experiment given in the above pharmacological experiment 5 clearly shows, each compound of the present invention has a remarkable inhibiting effect.

As the prostaglandin $E_2$ biosynthesis inhibition experiment given in the above pharmacological experiment 6 clearly shows, each compound of the present invention further has a remarkable inhibiting effect as compared with the comparative drug.

As the 5-HETE biosynthesis inhibition experiment given in the above pharmacological experiment 7 clearly shows, the compound of the present invention furthermore has a remarkable inhibiting effect.

Thus it has been found out that the compound of the present invention has highly specific and remarkable pharmacological activities in the comparative pharmacological experiments with indomethacin which is a typical nonsteroidal drug with potent effects.

Accordingly, the compound of the present invention is promising as an antirheumatic agent for various diseases accompanied by inflammation or pain, thus being highly useful in the pharmaceutical industry.

What is claimed is:

1. A diphenylthiazole derivative represented by the following general formula (1).

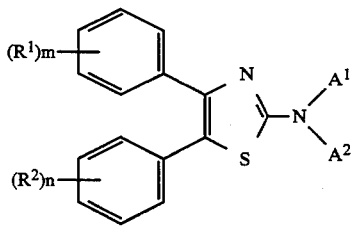 (I)

wherein m and n are each 1 or 2; $R^1$ and $R^2$ represent each a hydrogen atom, a lower alkyl group, a lower alkoxy group, a lower alkylsulfenyl group, a nitro group, an amino group, a methanesulfonyloxy group or a halogen atom; $A^1$ represents a lower alkanesulfonyl group, a halogenated lower alkanesulfonyl group, a substituted benzenesulfonyl group, and $A^2$ represents a hydrogen atom, a lower alkanesulfonyl group, a halogenated lower alkanesulfonyl group or a lower alkyl group, or a pharmaceutically acceptable salt thereof.

2. The compound according to claim 1 which is 2-trifluoromethanesulfonylamino-4,5-diphenylthiazole.

3. The compound according to claim 1 which is 5-(4-methoxyphenyl)2-trifluoromethanesulfonylamino-4,5-diphenylthiazole.

4. The compound according to claim 1 which is 4(4-nitro-phenyl)2-trifluoromethanesulfonylamino-4,5-diphenylthiazole.

5. The compound according to claim 1 which is 4-(4-methoxyphenyl)2-trifluoromethanesulfonylamino-4,5-diphenylthiazole.

6. The compound according to claim 1 which is 4-(4-fluorophenyl)2-trifluoromethanesulfonylamino-4,5-diphenylthiazole.

* * * * *